(12) United States Patent
Simpson et al.

(10) Patent No.: US 7,081,195 B2
(45) Date of Patent: Jul. 25, 2006

(54) SYSTEMS AND METHODS FOR IMPROVING ELECTROCHEMICAL ANALYTE SENSORS

(75) Inventors: Peter Simpson, Del Mar, CA (US); James Brauker, San Diego, CA (US); Victoria Carr-Brendel, Pleasanton, CA (US); Paul Goode, Cherry Hill, NJ (US); Mark Tapsak, Orangeville, PA (US)

(73) Assignee: DexCom, inc., San Diego, CA (US)

( * ) Notice: Subject to any disclaimer, the term of this patent is extended or adjusted under 35 U.S.C. 154(b) by 0 days.

(21) Appl. No.: 11/007,635

(22) Filed: Dec. 7, 2004

(65) Prior Publication Data

US 2005/0161346 A1    Jul. 28, 2005

Related U.S. Application Data

(60) Provisional application No. 60/527,892, filed on Dec. 8, 2003, provisional application No. 60/587,787, filed on Jul. 13, 2004, provisional application No. 60/614,683, filed on Sep. 30, 2004.

(51) Int. Cl.
*G01N 27/327* (2006.01)

(52) U.S. Cl. .............. 205/777.5; 205/792; 204/403.01; 204/403.11

(58) Field of Classification Search ................ 205/775, 205/777.5, 792; 204/403.01, 403.11, 406
See application file for complete search history.

(56) References Cited

U.S. PATENT DOCUMENTS

| | | | |
|---|---|---|---|
| 3,966,580 A | 6/1976 | Janata et al. | |
| 3,979,274 A | 9/1976 | Newman | |
| 4,040,908 A | 8/1977 | Clark, Jr. | |
| 4,073,713 A | 2/1978 | Newman | |
| 4,172,770 A | 10/1979 | Semersky et al. | |
| 4,388,166 A | 6/1983 | Suzuki et al. | |
| 4,415,666 A | 11/1983 | D'Orazio et al. | |
| 4,418,148 A | 11/1983 | Oberhardt | |
| 4,436,094 A | 3/1984 | Cerami | |
| 4,484,987 A | 11/1984 | Gough | |
| 4,534,355 A | 8/1985 | Potter | |
| 4,650,547 A | 3/1987 | Gough | |
| 4,663,824 A | 5/1987 | Kenmochi | |
| 4,671,288 A | 6/1987 | Gough | |
| 4,686,044 A | 8/1987 | Behnke et al. | |
| 4,689,309 A | 8/1987 | Jones | |
| 4,703,756 A | 11/1987 | Gough et al. | |
| 4,750,496 A * | 6/1988 | Reinhart et al. | ............ 600/347 |
| 4,757,022 A | 7/1988 | Shults et al. | |

(Continued)

FOREIGN PATENT DOCUMENTS

EP    0 107 634    5/1984

(Continued)

OTHER PUBLICATIONS

Bard et al, Electrochemical Methods, 1980, pp. 173-175.*

(Continued)

*Primary Examiner*—Kaj K. Olsen
(74) *Attorney, Agent, or Firm*—Knobbe, Martens, Olson & Bear, LLP

(57) ABSTRACT

An analyte-measuring device, particularly an electrochemical sensor, is provided for measuring current values at multiple bias potential settings to assess the quality of the analyte measurement, identify interference in the signal, and calculate substantially interference-free analyte concentration measurements. The device and method are suitable for calculating substantially interference-free analyte concentration measurements when glucose is the analyte and acetaminophen is an interfering species.

42 Claims, 3 Drawing Sheets

U.S. PATENT DOCUMENTS

| | | | |
|---|---|---|---|
| 4,759,828 A | 7/1988 | Young et al. | |
| 4,776,944 A | 10/1988 | Janata et al. | |
| 4,781,798 A | 11/1988 | Gough | |
| 4,810,470 A | 3/1989 | Burkhardt et al. | |
| 4,861,830 A | 8/1989 | Ward, Jr. | |
| 4,871,440 A | 10/1989 | Nagata et al. | |
| 4,890,620 A | 1/1990 | Gough | |
| 4,927,407 A | 5/1990 | Dorman | |
| 4,963,595 A | 10/1990 | Ward et al. | |
| 4,994,167 A | 2/1991 | Shults et al. | |
| 5,030,333 A | 7/1991 | Clark, Jr. | |
| 5,034,112 A * | 7/1991 | Murase et al. | 204/406 |
| 5,140,985 A | 8/1992 | Schroeder et al. | |
| 5,165,407 A | 11/1992 | Wilson et al. | |
| 5,171,689 A | 12/1992 | Kawaguri et al. | |
| 5,235,003 A | 8/1993 | Ward et al. | |
| 5,322,063 A | 6/1994 | Allen et al. | |
| 5,352,351 A * | 10/1994 | White et al. | 204/403.04 |
| 5,356,786 A | 10/1994 | Heller et al. | |
| 5,397,848 A | 3/1995 | Yang et al. | |
| 5,411,647 A | 5/1995 | Johnson et al. | |
| 5,428,123 A | 6/1995 | Ward et al. | |
| 5,431,160 A | 7/1995 | Wilkins | |
| 5,476,094 A | 12/1995 | Allen et al. | |
| 5,496,453 A | 3/1996 | Uenoyama et al. | |
| 5,497,772 A | 3/1996 | Schulman et al. | |
| 5,540,828 A | 7/1996 | Yacynych | |
| 5,575,930 A | 11/1996 | Tietje-Girault et al. | |
| 5,589,563 A | 12/1996 | Ward et al. | |
| 5,683,562 A | 11/1997 | Schaffar et al. | |
| 5,711,861 A | 1/1998 | Ward et al. | |
| 5,756,632 A | 5/1998 | Ward et al. | |
| 5,776,324 A | 7/1998 | Usala | |
| 5,777,060 A | 7/1998 | Van Antwerp | |
| 5,783,054 A | 7/1998 | Raguse et al. | |
| 5,791,344 A | 8/1998 | Schulman et al. | |
| 5,795,774 A | 8/1998 | Matsumoto et al. | |
| 5,871,514 A | 2/1999 | Wiklund et al. | |
| 5,882,494 A | 3/1999 | Van Antwerp | |
| 5,897,578 A | 4/1999 | Wiklund et al. | |
| 5,910,554 A | 6/1999 | Kempe et al. | |
| 5,919,215 A | 7/1999 | Wiklund et al. | |
| 5,964,261 A | 10/1999 | Neuenfeldt et al. | |
| 5,965,380 A | 10/1999 | Heller et al. | |
| 5,985,129 A | 11/1999 | Gough et al. | |
| 6,001,067 A | 12/1999 | Shults et al. | |
| 6,011,984 A | 1/2000 | Van Antwerp et al. | |
| 6,016,448 A | 1/2000 | Busacker et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,103,033 A | 8/2000 | Say et al. | |
| 6,107,083 A | 8/2000 | Collins et al. | |
| 6,119,028 A | 9/2000 | Schulman et al. | |
| 6,121,009 A | 9/2000 | Heller et al. | |
| 6,134,461 A | 10/2000 | Say et al. | |
| 6,144,869 A | 11/2000 | Berner et al. | |
| 6,162,611 A | 12/2000 | Heller et al. | |
| 6,200,772 B1 | 3/2001 | Vadgama et al. | |
| 6,214,185 B1 | 4/2001 | Offenbacher et al. | |
| 6,241,863 B1 | 6/2001 | Monbouquette | |
| 6,259,937 B1 | 7/2001 | Schulman et al. | |
| 6,274,285 B1 | 8/2001 | Gries et al. | |
| 6,329,161 B1 | 12/2001 | Heller et al. | |
| 6,330,464 B1 | 12/2001 | Colvin, Jr. et al. | |
| 6,343,225 B1 | 1/2002 | Clark, Jr. | |
| 6,356,776 B1 | 3/2002 | Berner et al. | |
| 6,368,274 B1 | 4/2002 | Van Antwerp et al. | |
| 6,372,244 B1 | 4/2002 | Antanavich et al. | |
| 6,400,974 B1 | 6/2002 | Lesho | |
| 6,409,674 B1 | 6/2002 | Brockway et al. | |
| 6,454,710 B1 | 9/2002 | Ballerstadt et al. | |
| 6,466,810 B1 | 10/2002 | Ward et al. | |
| 6,477,395 B1 | 11/2002 | Schulman et al. | |
| 6,484,046 B1 | 11/2002 | Say et al. | |
| 6,546,268 B1 | 4/2003 | Ishikawa et al. | |
| 6,560,471 B1 | 5/2003 | Heller et al. | |
| 6,565,509 B1 | 5/2003 | Say et al. | |
| 6,613,379 B1 | 9/2003 | Ward et al. | |
| 6,615,078 B1 | 9/2003 | Burson et al. | |
| 6,618,934 B1 | 9/2003 | Feldman et al. | |
| 6,642,015 B1 | 11/2003 | Vachon et al. | |
| 6,654,625 B1 | 11/2003 | Say et al. | |
| 6,702,857 B1 | 3/2004 | Brauker et al. | |
| 6,721,587 B1 | 4/2004 | Gough | |
| 6,741,877 B1 | 5/2004 | Shults et al. | |
| 6,862,465 B1 | 3/2005 | Shults et al. | |
| 6,892,085 B1 | 5/2005 | McIvor et al. | |
| 6,895,263 B1 | 5/2005 | Shin et al. | |
| 2003/0032874 A1 | 2/2003 | Rhodes et al. | |
| 2003/0070548 A1 | 4/2003 | Clausen | |
| 2003/0188427 A1 | 10/2003 | Say et al. | |
| 2003/0217966 A1 | 11/2003 | Tapsak et al. | |
| 2004/0045879 A1 | 3/2004 | Shults et al. | |
| 2004/0106857 A1 | 6/2004 | Gough | |
| 2004/0219664 A1 | 11/2004 | Heller et al. | |
| 2005/0027180 A1 | 2/2005 | Goode et al. | |
| 2005/0027181 A1 | 2/2005 | Goode et al. | |
| 2005/0027463 A1 | 2/2005 | Goode et al. | |
| 2005/0031689 A1 | 2/2005 | Shults et al. | |
| 2005/0033132 A1 | 2/2005 | Shults et al. | |
| 2005/0043598 A1 | 2/2005 | Goode et al. | |
| 2005/0051427 A1 | 3/2005 | Brauker et al. | |
| 2005/0051440 A1 | 3/2005 | Simpson et al. | |
| 2005/0054909 A1 | 3/2005 | Petisce et al. | |
| 2005/0056552 A1 | 3/2005 | Simpson et al. | |
| 2005/0090607 A1 | 4/2005 | Tapsak et al. | |
| 2005/0112169 A1 | 5/2005 | Brauker et al. | |
| 2005/0192557 A1 | 9/2005 | Brauker et al. | |

FOREIGN PATENT DOCUMENTS

| | | |
|---|---|---|
| EP | 0 535 898 | 4/1993 |
| EP | 0 817 809 B1 | 1/1998 |
| EP | 0 885 932 A2 | 12/1998 |
| FR | 2 656 423 | 6/1991 |
| GB | 1 442 303 | 7/1976 |
| JP | 62083649 | 4/1987 |
| WO | WO 90/00738 | 1/1990 |
| WO | WO 92/13271 | 8/1992 |
| WO | WO 94/22367 | 10/1994 |
| WO | WO 96/30431 | 10/1996 |
| WO | WO 99/58051 | 11/1999 |
| WO | WO 00/13003 | 3/2000 |
| WO | WO 00/59373 | 10/2000 |
| WO | WO 01/20334 A1 | 3/2001 |
| WO | WO 01/58348 A2 | 8/2001 |
| WO | WO 01/68901 A2 | 9/2001 |
| WO | WO 01/88524 A1 | 11/2001 |
| WO | WO 02/053764 | 7/2002 |

OTHER PUBLICATIONS

Baker, et al. 1993. Dynamic concentration challenges for biosensor characterization. *Biosensors & Bioelectronics*, 8:433-441.

Bindra, et al. 1989. Pulsed amperometric detection of glucose in biological fluids at a surface-modified gold electrode. *Anal Chem*, 61:2566-2570.

Bisenberger, et al. 1995. A triple-step potential waveform at enzyme multisensors with thick-film gold electrodes for detection of glucose and sucrose. *Sensors and Actuators*, B 28:181-189.

Cai, Q.; Zeng, K.; Ruan, C.; Desai, T. A.; Grimes, C. A. A wireless, remote query glucose biosensor based on a pH-sensitive polymer. *Anal Chem* 2004, 76, 4038-4043.

Chen, et al. 2002. Defining the period of recovery of the glucose concentration after its local perturbation by the implantation of a miniature sensor. *Clin. Chem. Lab. Med.*, 40:786-789.

Choleau, et al. 2002. Calibration of a subcutaneo amperometric glucose sensor. Part 1. Effect of measurement uncertainties on the determination of sensor sensitivity and background current. *Biosensors and Bioelectronics*, 17:641-646.

Csöregi, et al. 1994. Amperometric microbiosensors for detection of hydroen peroxide and glucose based on peroxidase-modified carbon fibers. *Electroanalysis*, 6:925-933.

D'Arrigo, et al. Poro -Si based bioreactors for glucose monitoring and drugs production. *Proc. of SPIE* 2003, 4982, 178-184.

Dixon, et al. 2002. Characterization in vitro and in vivo of the oxygen dependence of an enzyme/polymer biosensor for monitoring brain glucose. *Journal of Neuroscience Methods*, 119:135-142.

Ernst, et al. 2002. Reliable glucose monitoring through the e of microsystem technology. *Anal. Bioanal. Chem.*, 373:758-761.

Fare, et al. 1998. Functional characterization of a conducting polymer-based immunoassay system. *Biosensors & Bioelectronics*, 13(3-4):459-470.

Feldman, AB.; Brazg, R.; Schwartz, S.; Weinstein, R. A continuo glucose sensor based on wired enzyme technology—results from a 3-day trial in patients with type 1 diabetes. *Diabetes Technol Ther* 2003, 5, 769-779.

Garg, S.; Schwartz, S.; Edelman, S. Improved Glucose Excursions ing an Implantable Real-Time Continuo Glucose Sensor in Adults with Type I Diabetes. *Diabetes Care* 2004, 27, 734-738.

Gilligan, et al. 1994. Evaluation of a subcutaneous glucose sensor out to 3 months in a dog model. *Diabetes Care*, 17(8):882-887.

Gilligan, B. D.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. *Diabetes Technol Ther* 2004, 6, 378-386.

Gough, et al. 2000. Immobilized glucose oxidase in implantable glucose sensor technology. *Diabetes Technology & Therapeutics*, 2(3):377-380.

Hall, et al. 1998. Electrochemical oxidation of hydrogen peroxide at platinum electrodes. Part 1. An adsorption-controlled mechanism. *Electrochimica Acta*, 43(5-6):579-588.

Hall, et al. 1998. Electrochemical oxidation of hydrogen peroxide at platinum electrodes. Part II: Effect of potential. *Electrochimica Acta*, 43(14-15):2015-2024.

Hall, et al. 1999. Electrochemical oxidation of hydrogen peroxide at platinum electrodes. Part III: Effect of temperature. *Electrochimica Acta*, 44:2455-2462.

Hall, et al. 1999. Electrochemical oxidation of hydrogen peroxide at platinum electrodes. Part IV: Phosphate buffer dependence. *Electrochimica Acta*, 44:4573-4582.

Hall, et al. 2000. Electrochemical oxidation of hydrogen peroxide at platinum electrodes. Part V: Inhibition by chloride. *Electrochimica Acta*, 45:3573-3579.

Heller, A. Implanted electrochemical glucose sensors for the management of diabetes. *Annu Rev Biomed Eng* 1999, 1, 153-175.

Heller, A. Plugging metal connectors into enzymes. *Nat Biotechnol* 2003, 21, 631-2.

Kang, S. K.; Jeong, R. A.; Park, S.; Chung, T. D.; Park, S.; Kim, H. C. In vitro and short-term in vivo characteristics of a Kel-F thin film modified glucose sensor. *Anal Sci* 2003, 19, 1481-1486.

Kargol, et al. Studies on the structural properties of porous membranes: measurement of linear dimensions of solutes. *Biophys Chem* 2001, 91, 263-271.

Lerner, et al. 1984. An implantable electrochemical glucose sensor. *Ann. N. Y. Acad. Sci.*, 428:263-278.

Leypoldt, et al. 1984. Model of a two-substrate enzyme electrode for glucose. *Anal. Chem.*, 56:2896-2904.

Moatti-Sirat, D.; Capron, F.; Poitout, V.; Reach, G.; Bindra, D. S.; Zhang, Y.; Wilson, G. S.; Thevenot, D. R. Towards continuo glucose monitoring: in vivo evaluation of a miniaturized glucose sensor implanted for several days in rat subcutaneo tissue. *Diabetologia* 1992, 35, 224-230.

Moatti-Sirat, et al., *Evaluating in vitro and in vivo the interference of ascorbate and acetaminophen on glucose detection by a needle-type glucose sensor*, 1992, Elsevier Science Publishers Ltd. pp. 345-352.

Moussy, et al. 1994. A miniaturized Nafion-based glucose sensor: *In vitro* and *in vivo* evaluation in dogs. *Int. J. Artif. Organs*, 17(2):88-94.

Myler, et al. Ultra-thin-polysiloxane-film-composite membranes for the optimisation of amperometric oxidase enzyme electrodes. *Biosens Bioelectron* 2002, 17, 35-43.

Ohara, T. J.; Rajagopalan, R.; Heller, A. "Wired" enzyme electrodes for amperometric determination of glucose or lactate in the presence of interfering substances. *Anal Chem* 1994, 66, 2451-2457.

Palmisano, et al. 2000. Simultaneous monitoring of glucose and lactate by an interferance and cross-talk free dual electrode amperometric biosensor based on electropolymerized thin films. *Biosensors & Bioelectronics*, 15:531-539.

Poitout, et al. 1993. A glucose monitoring system for on line estimation in man of blood glucose concentration ing a miniaturized glucose sensor implanted in the subcutaneo tissue and a wearable control unit. *Diabetologia*, 36:658-663.

Rebrin, et al. 1999. Subcutaneous glucose predicts plasma glucose independent of insulin: Implications for continuo monitoring. *Am. J. Physiol.*, 277:E561-71.

Sansen, et al. 1990. A smart sensor for the voltammetric measurement of oxygen or glucose concentrations. *Sensors and Actuators*, B 1:298-302.

Schuler, R.; Wittkampf, M.; Chemniti, G. C. Modified gas-permeable silicone rubber membranes for covalent immobilisation of enzymes and their use in biosensor development. *Analyst* 1999, 124, 1181-1184.

Shichiri, M.; Kawamori, R.; Yamasaki, Y.; Hakui, N.; Abe, H. Wearable artificial endocrine pancrease with needle-type glucose sensor. *Lancet* 1982, 2, 1129-1131.

Shichiri, et al. 1986. Telemetry glucose monitoring device with needle-type glucose sensor: A useful tool for blood glucose monitoring in diabetic individuals. *Diabetes Care*, 9(3):298-301.

Shichiri, M.; Kawamori, R.; Yamasaki, Y.; Hakui, N.; Asakawa, N.; Abe, H. Needle-type Glucose Sensor for Wearable Artificial Endocrine Pancreas. *Book Implantable Sensors* 1985, 197-210.

Sriyudthsak, M.; Cholapranee, T.; Sawadsaringkarn, M.; Yupongchaey, N.; Jaiwang, P. Enzyme-epoxy membrane based glucose analyzing system and medical applications. Biosens Bioelectron 1996, 11, 735-742.

Sternberg, R.; Barrau, M. AB.; Gangiotti, L.; Thevenot, D. R.; Bindra, D. S.; Wilson, G. S.; Velho, G.; Froguel, P.; Reach, G. Study and development of multilayer needle-type enzyme-based glucose microsensors. *Biosensors* 1989, 4, 27-40.

Updike, et al. 1967. The enzyme electrode. *Nature*, 214:986-988.

Updike, et al. 1979. Continuous glucose monitor based on a immobilized enzyme electrode detector. *J Lab Clin Med*, 93(4):518-527.

Updike, et al. 1982. Implanting the glucose enzyme electrode: Problems, progress, and alternative solutions. *Diabetes Care*, 5(3):207-212.

Updike et al. 1994. Improved long-term performance *in vitro* and *in vivo*. *ASAIO Journal*, 40(2):157-163.

Updike et al. 1997. Principles of long-term fully implanted sensors with emphasis on radiotelemtric monitoring of blood glucose from inside a subcutaneous foreign body capsule (FBC). In Fraser, D. M. (Ed.). Biosensors in the Body: Continuous *in vivo* Monitoring. Chap. 4, pp. 117-137, Hoboken, NJ: John Wiley.

Updike, et al. 2000. A subcutaneous glucose sensor with improved longevity, dynamic range, and stability of calibration. *Diabetes Care*, 23(2):208-214.

Valdes, et al. 2000. In vitro and in vivo degradation of glucose oxidase enzyme used for an implantable glucose biosensor. *Diabetes Technol. Ther.*, 2:367-376.

Velho. G.; Froguel, P.; Sternberg, R.; Thevenot, D. R.; Reach, G. In vitro and in vivo stability of electrode potentials in needle-type glucose sensors. Influence of needle material. Diabetes 1989, 38, 164-171.

Wang, J.; Liu, J.; Chen, L.; Lu, F. Highly Selective Membrane-Free, Mediator-Free Glucose Biosensor. Anal. Chem. 1994, 66, 3600-3603.

Wilkins, E.; Atanasov, P. Glucose monitoring: state of the art and future possibilities. Med Eng Phys 1995, 18, 273-288.

Wilson, et al. 1992. Progress toward the development of an implantable sensor for glucose. *Clin. Chem.*, 38(9):1613-1617.

Wilson, et al. 2000. Enzyme-based biosensors for in vivo measurements. *Chem. Rev.*, 100:2693-2704.

Yang, et al. 1998. Development of needle-type glucose sensor with high selectivity. *Science and Actuators*,B 46:249-256.

Zhang, et al. 1994. Elimination of the acetaminophen interference in an implantable glucose sensor. *Analytical Chemistry*, 66(7):1183-1188.

U.S. Appl. No. 09/447,227, filed Nov. 22, 1999.
U.S. Appl. No. 10/838,909, filed May 3, 2004.
U.S. Appl. No. 10/838,912, filed May 3, 2004.
U.S. Appl. No. 10/838,658, filed May 3, 2004.
U.S. Appl. No. 10/885,476, filed Jul. 6, 2004.

Tierney, et al., "Effect of Acetaminophen on the Accuracy of Glucose Measurements Obtained with the GlucoWatch Biographer," *Diabetes Technology & Therapeutcis* 2(2):199-207, 2000.

* cited by examiner

SYSTEMS AND METHODS FOR IMPROVING ELECTROCHEMICAL ANALYTE SENSORS

RELATED APPLICATIONS

This application claims the benefit of priority under 35 U.S.C. § 119(e) to U.S. Provisional Application No. 60/527892, filed Dec. 8, 2003, U.S. Provisional Application 60/587787, filed Jul. 13, 2004, and U.S. Provisional Application 60/614683, filed Sep. 30, 2004. All above-referenced prior applications are incorporated by reference herein in their entirety.

FIELD OF THE INVENTION

The present invention relates generally to systems and methods involving the electrochemical detection or measurement of analytes.

BACKGROUND OF THE INVENTION

A variety of sensors are known that use an electrochemical cell to provide output signals by which the presence or absence of an analyte in a sample can be determined. For example in an electrochemical cell, an analyte (or a species derived from it) that is electro-active generates a detectable signal at an electrode, and this signal can be used to detect or measure the presence and/or amount within a biological sample. In some conventional sensors, an enzyme is provided that reacts with the analyte to be measured, and the byproduct of the reaction is qualified or quantified at the electrode. An enzyme has the advantage that it can be very specific to an analyte and also, when the analyte itself is not sufficiently electro-active, can be used to interact with the analyte to generate another species which is electro-active and to which the sensor can produce a desired output. In one conventional amperometric glucose oxidase-based glucose sensor, immobilized glucose oxidase catalyses the oxidation of glucose to form hydrogen peroxide, which is then quantified by amperometric measurement (for example, change in electrical current) through a polarized electrode.

One problem with electrochemical sensors is that they can electrochemically react not only with the analyte to be measured (or by-product of the enzymatic reaction with the analyte), but additionally can react with other electroactive species that are not intentionally being measured (for example, interfering species), which causes an increase in signal strength due to these "interfering species". In other words, interfering species are compounds with an oxidation or reduction potential that overlaps with the analyte to be measured (or by product of the enzymatic reaction with the analyte). For example, in a conventional amperometric glucose oxidase-based glucose sensor wherein the sensor measures hydrogen peroxide, interfering species such as acetaminophen, ascorbate, and urate, are known to produce inaccurate signal strength when they are not properly controlled. Moreover, signal interference can result from effects, such as local ischemia, or the like, which cause the signal to produce erroneous output.

Some glucose sensors utilize a membrane system that blocks at least some interfering species, such as ascorbate and urate. In some such examples, at least one layer of the membrane assembly includes a porous structure that has a relatively impermeable matrix with a plurality of "micro holes" or pores of molecular dimensions, such that transfer through these materials is primarily due to passage of species through the pores (for example, the layer acts as a microporous barrier or sieve blocking interfering species of a particular size). In other such examples, at least one layer of the membrane assembly defines a permeability that allows selective dissolution and diffusion of species as a solute through the layer. Unfortunately, it is difficult to find membranes that are satisfactory or reliable in use, especially in vivo, which effectively block all interferants and/or interfering species.

SUMMARY OF THE INVENTION

Accordingly, the preferred embodiments provide systems and methods for improving the quality of analyte-measuring devices by identifying interfering species on an analyte signal. The preferred embodiments further provide systems and methods for reducing or eliminating the effects of interfering species on an analyte signal by obtaining differential measurements based on multiple bias potential settings.

In a first embodiment, a method for identifying an interfering species using an analyte-measuring device is provided, the method comprising providing at least one electrochemical sensor; measuring a first signal output obtained at a first bias potential setting; measuring a second signal output obtained at a second bias potential setting; and comparing the first signal output with the second signal output to determine a differential measurement, thereby identifying a presence of an interfering species in a liquid.

In an aspect of the first embodiment, the interfering species is negatively identified when the differential measurement is below a set threshold.

In an aspect of the first embodiment, the interfering species is positively identified when the differential measurement is above a set threshold.

In an aspect of the first embodiment, the method further comprises calculating an analyte concentration from the differential measurement, wherein the step of calculating is performed when interfering species are positively identified.

In an aspect of the first embodiment, the sensor is configured to switch between the first bias potential setting and the second bias potential setting.

In an aspect of the first embodiment, the step of providing comprises providing a first sensor at the first bias potential setting and a second sensor at the second bias potential setting.

In an aspect of the first embodiment, the interfering species is acetaminophen.

In an aspect of the first embodiment, the analyte measuring device is a glucose sensor.

In an aspect of the first embodiment, the liquid comprises blood.

In an aspect of the first embodiment, the liquid is a bodily fluid, such as interstitial fluid.

In an aspect of the first embodiment, the method further comprises deriving an analyte concentration from the first signal output and the second signal output to determine an analyte concentration.

In a second embodiment, an analyte-measuring device for measuring a concentration of an analyte and identifying an interfering species is provided, the device comprising at least one electrochemical sensor configured to provide a differential measurement of a current output signal at a first bias potential and at a second bias potential, wherein the differential measurement is employed to identify a species interfering with the analyte concentration.

In an aspect of the second embodiment, the electrochemical sensor is configured to switch between the first bias potential setting and the second bias potential setting.

In an aspect of the second embodiment, the device further comprises a first sensor at the first bias potential setting and a second sensor at the second bias potential setting.

In an aspect of the second embodiment, the analyte comprises glucose and the interfering species comprises acetaminophen.

In a third embodiment, a method for identifying a signal interference in an analyte-measuring device is provided, the method comprising providing at least one electrochemical sensor; measuring a first signal output obtained at a first bias potential setting; measuring a second signal output at a second bias potential setting; comparing the first signal output with the second signal output to determine a differential measurement, thereby identifying an interference in the signal outputs.

In an aspect of the third embodiment, the method further comprises deriving an analyte concentration from the first signal output and the second signal output to determine an analyte concentration.

In an aspect of the third embodiment, the method further comprises measuring a third signal output at a third bias potential setting indicative of an additional interference in the signal outputs.

In an aspect of the third embodiment, the analyte comprises glucose and the interfering species comprises acetaminophen.

In a fourth embodiment, an analyte-measuring device for measuring a concentration of analyte and identifying interference in signal output is provided, the device comprising the device comprising at least one electrochemical sensor configured to provide a differential measurement of a current output signal at a first bias potential setting and at a second bias potential setting, whereby an interference within the analyte concentration measurement signal is determined.

In an aspect of the fourth embodiment, the device is configured to derive an analyte concentration from the measurements at the first potential bias setting and at the second bias potential setting.

In an aspect of the fourth embodiment, the analyte comprises glucose and the interfering species comprises acetaminophen.

DETAILED DESCRIPTION OF THE PREFERRED EMBODIMENT

Figure 1:
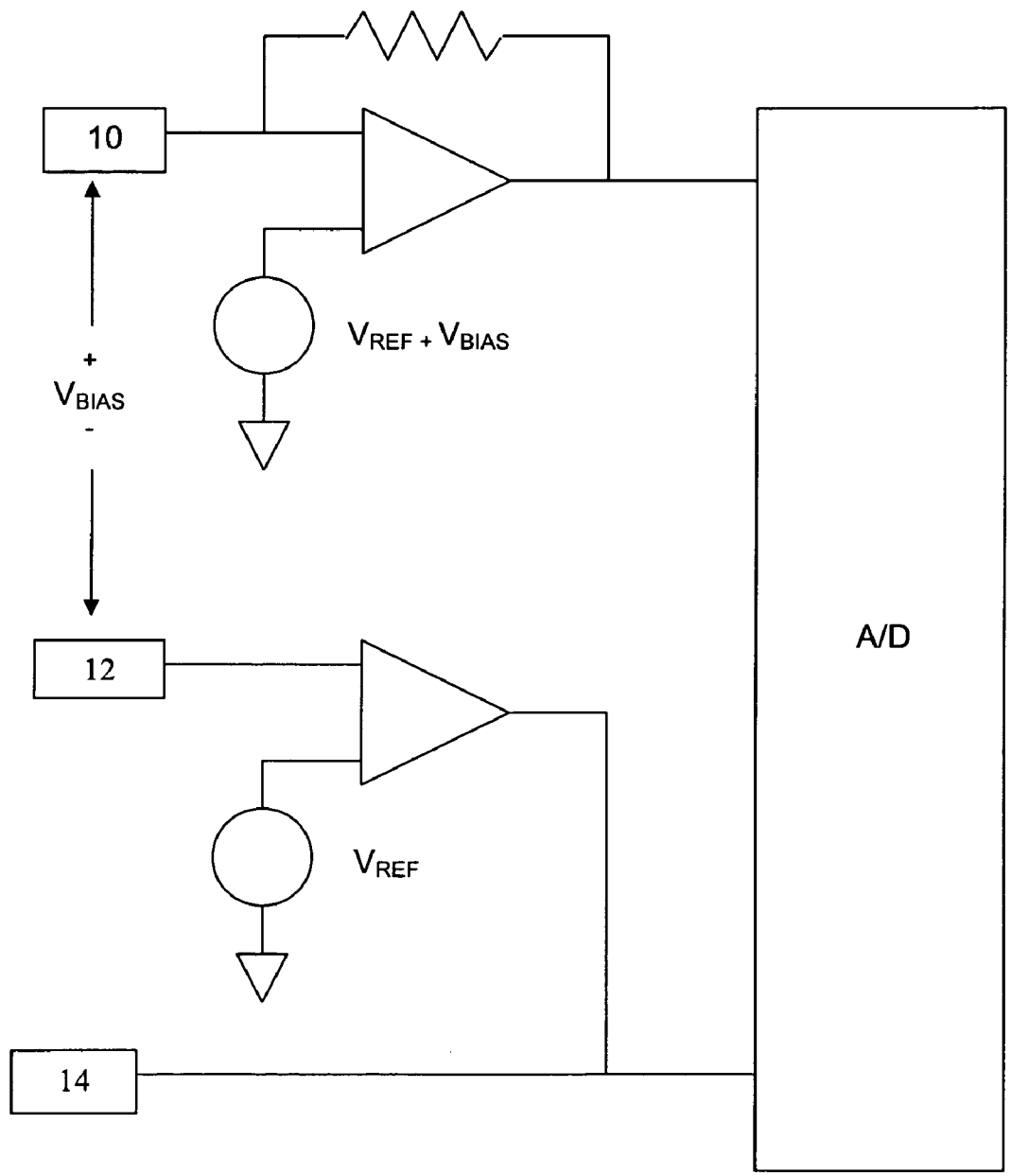
FIG. 1 is a circuit diagram of a potentiostat that controls a typical three-electrode system.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "sensor," as used herein, is a broad term and is used in its ordinary sense, including, without limitation, the portion or portions of an analyte-monitoring device that detect an analyte. In one embodiment, the sensor includes an electrochemical cell that has a working electrode (anode), a reference electrode and a counter electrode (cathode) passing through and secured within the sensor body forming an electrochemically reactive surface at one location on the body, an electronic connection at another location on the body, and a membrane system affixed to the body and covering the electrochemically reactive surface. The counter electrode typically has a greater electrochemically reactive surface area than the working electrode. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The term "signal output," as used herein, is a broad term and is used in its ordinary sense, including, without limitation, an analog or digital signal directly related to the measured analyte from the analyte-measuring device. The term broadly encompasses a single point, or alternatively, a plurality of time spaced data points from a substantially continuous glucose sensor, which comprises individual measurements taken at time intervals ranging from fractions of a second up to, for example, 1, 2, or 5 minutes or longer.

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "potentiostat," as used herein, is a broad term and is used in its ordinary sense, including, without limitation, an electrical system that controls the potential between the working and reference electrodes of a three-electrode cell at a preset value independent of resistance changes between the electrodes. It forces whatever current is necessary to flow between the working and counter electrodes to keep the desired potential, as long as the needed cell voltage and current do not exceed the compliance limits of the potentiostat.

The term "bias potential," as used herein, is a broad term and is used in its ordinary sense, including, without limitation, the voltage difference between two points in a circuit, which is the cause of the flow of a current, if sufficient analyte is present.

The term "differential measurement," as used herein, is a broad term and is used in its ordinary sense, including, without limitation, the difference between multiple signal output measurements at different bias potential settings.

The terms "interferants" and "interfering species," as used herein, are broad terms and are used in their ordinary sense, including, without limitation, effects and/or species that interfere with the measurement of an analyte of interest in a sensor to produce a signal that does not accurately represent the analyte measurement. In one example of an electrochemical sensor, interfering species are compounds with an oxidation or reduction potential that overlaps with the analyte to be measured. In another example of an enzyme-based electrochemical sensor, local ischemia is an interferant that produces error in the output signal due to lack of sufficient oxygen to react with the enzyme.

Overview

The preferred embodiments relate to the use of an analyte-measuring device that measures a concentration of analyte or a substance indicative of the concentration or presence of the analyte. In some embodiments, the analyte-measuring device measures glucose, lactate, oxygen, or the like. In some embodiments, the analyte-measuring device is a continuous device, for example a subcutaneous, transdermal, or intravascular device. In some embodiments, the device can analyze a plurality of intermittent blood samples. In some embodiments, the device can analyze a single blood sample. The analyte-measuring device can use any method of analyte-measurement, including enzymatic, chemical, physical, electrochemical, or the like.

The analyte-measuring device uses any known method, including invasive, minimally invasive, and non-invasive sensing techniques, to provide an output signal indicative of the concentration of the analyte. The output signal is typically a raw signal that is used to provide a useful value of the analyte to a user, such as a patient or doctor, who may be using the device.

In one embodiment, the analyte-measuring device measures glucose using a transcutaneous glucose sensor, such as described in co-pending U.S. Provisional Patent Application Nos. 60/587,787 and 60/614,683. In another embodiment, the analyte-measuring device measures glucose using an electrochemical cell with a membrane system, such as described in U.S. Pat. No. 6,001,067 and U.S. Published Patent Application 2003/0032874, both of which are incorporated by reference herein in their entirety. In this embodiment, the membrane system provides an interference domain including a thin membrane that can limit diffusion of high molecular weight species. The interference domain serves to allow certain analytes and other substances that are to be measured by the electrodes to pass through, while preventing passage of other substances, including interfering species, such as ascorbate and urate. In one exemplary embodiment, the interference domain is constructed from polyurethane and has a thickness of about 0.1 to 5 microns. Although the interference domain does successfully block some interfering species described above, it does not sufficiently block other interfering species, such as acetaminophen.

4-Acetaminophenol (4-AAP, common name acetaminophen or paracetamol) is a nonprescription medication useful in the treatment of mild pain or fever, for example, acetaminophen can be found in Tylenol®. Acetaminophen is a commonly taken medication, and when ingested, can cause transient, non-glucose related signal artifacts in a glucose-measurement device. It is noted that much of the description of the preferred embodiments focuses on identifying acetaminophen, a known interfering species in the art of amperometric glucose sensors because it generates a positive signal independent of glucose concentration (for example, when measuring hydrogen peroxide). However, the preferred embodiments can be implemented to identify numerous other known interfering species in other known electrochemically-based analyte-measuring devices.

Description

FIG. 1 is a circuit diagram of a conventional potentiostat that controls a typical three-electrode system of an electrochemical cell, which can be employed with an electrochemical sensor such as described above. The potentiostat includes a working electrode 10, a reference electrode 12, and a counter electrode 14. Conventionally, the voltage applied to the working electrode 10 is a constant value (for example, +1.2V with respect to battery ground) and the voltage applied to the reference electrode 12 is also set at a constant value (for example, +0.6V with respect to battery ground) such that the bias potential ($V_{BIAS}$) applied between the working and reference electrodes is set at a constant value (for example, +0.6V). The counter electrode is configured to have a constant current (equal to the current being measured by the working electrode), which is accomplished by driving the voltage at the counter electrode 14 to a potential that balances the current going through the working electrode 10 such that current does not pass through the reference electrode 12. In addition, the counter electrode acts as a negative feedback circuit to maintain the desired voltage at the reference electrode.

In one embodiment of a glucose sensor such as described herein, a membrane system that contains glucose oxidase catalyzes the conversion of oxygen and glucose to hydrogen peroxide and gluconate, such as described above. Therefore, for each glucose molecule metabolized there is an equivalent change in molecular concentration in the co-reactant $O_2$ and the product $H_2O_2$. Consequently, one can use an electrode (for example, working electrode 10) to monitor the concentration-induced current change in either the co-reactant or the product (for example, $H_2O_2$) to determine glucose concentration. However, if an interfering species exists with an oxidation or reduction potential that overlaps with the co-reactant or the product (for example, $H_2O_2$), then the current change does not accurately reflect glucose concentration. Additionally, if an oxygen deficiency exists, such that insufficient oxygen is present to react with an analyte at the enzyme for example, then the current change similarly does not accurately reflect glucose concentration.

It is noted that a glucose sensor signal obtained from glucose when the bias potential is set between about +0.35V and about +0.75V is substantially constant under standard physiologic conditions. In contrast, a glucose sensor signal obtained from interfering species when the same bias potentials are set (between about +0.35V and about +0.75V) is not substantially constant under standard physiologic conditions. Current-voltage curves are known for various analytes and are available in the literature, for example such as described by Lerner, H.; Giner, J.; Soeldner, J. S.; Colton, C. K. An implantable electrochemical glucose sensor. *Ann N Y Acad Sci* 1984, 428, 263–278, which is incorporated herein by reference in its entirety.

Figure 2:
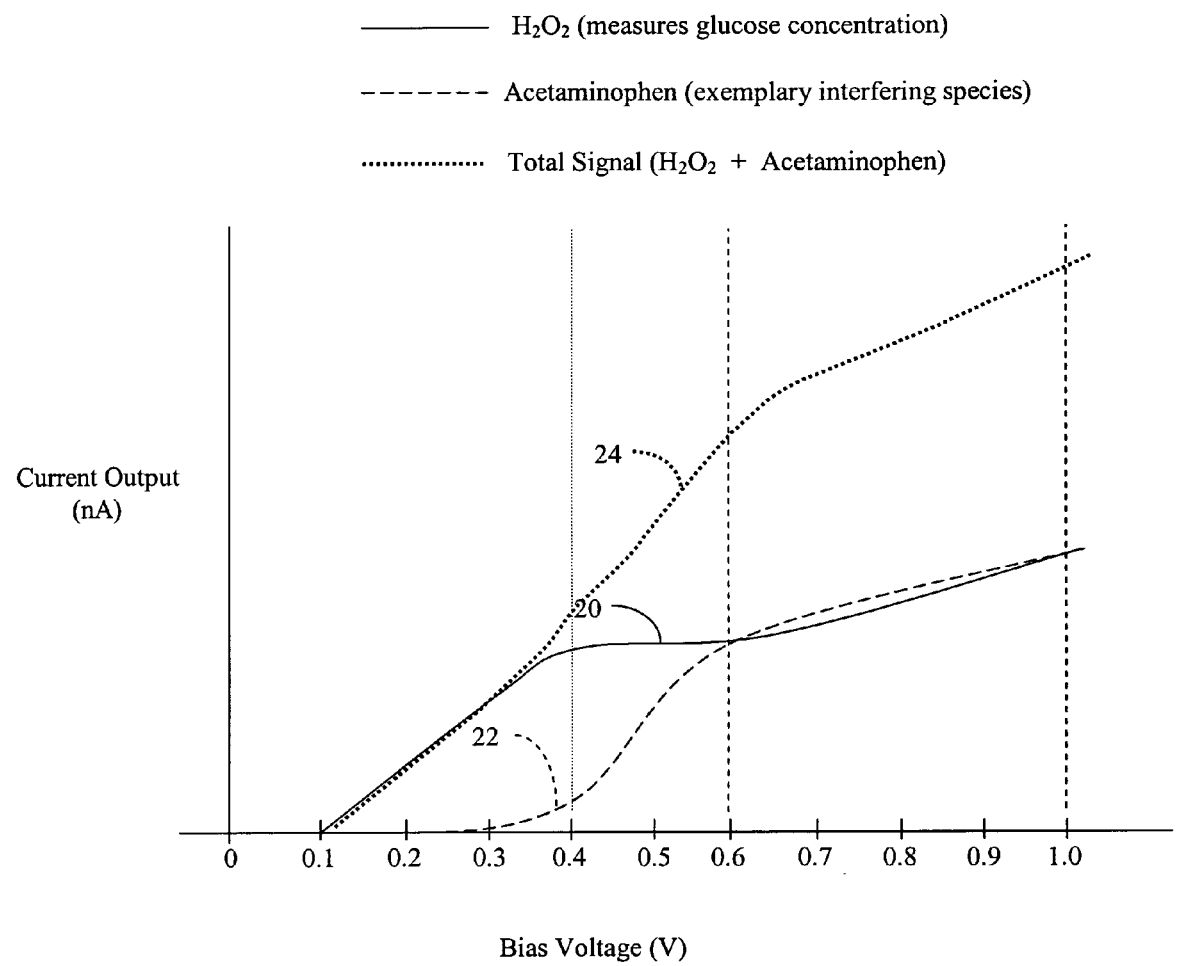
FIG. 2 is a schematic graph of current vs. voltage obtained from cyclic voltammetry of hydrogen peroxide and acetaminophen.

FIG. 2 is a schematic graph of current vs. voltage obtained from cyclic voltammetry (also known as a CV-curve) for hydrogen peroxide and acetaminophen. The x-axis represents bias potential applied to an electrochemical cell in Volts (V); the y-axis represents current output measured by the working electrode of the electrochemical cell in nano-Amps (nA). The schematic graph generally shows current output of an electrochemical enzyme-based glucose sensor as the bias potential is varied from about 0.1V to about 1.0V. Current output is shown without units because it is the differential response, rather than the actual measurement, of signal output that is being generally taught herein. As illustrated by the graph, acetaminophen 22 increases the total signal 24, resulting in an inaccurate glucose measurement that is significantly higher than the actual value.

The hydrogen peroxide curve 20 can be obtained by exposing an electrochemical sensor to glucose (without acetaminophen) and varying the bias potential from about 0.1V to about 1.0V. The graph shows the response of the glucose sensor to hydrogen peroxide; generally, the current increases at a relatively constant rate from about 0.1V to about 0.4V, after which it plateaus until about 0.6V, and then continues to increase at a slightly slower rate.

The acetaminophen curve 22 can be obtained by exposing an electrochemical sensor to acetaminophen (without glucose), and varying the bias potential from about 0.1V to about 1.0V. The graph shows the response of the glucose sensor to acetaminophen; generally, the acetaminophen curve 22 increases relatively slowly from about 0.1V to about 0.4V, showing a minimal current output of the acetaminophen signal (at 0.4V) relative to the higher glucose signal (at 4.0V). From 0.4V to 0.6V, the acetaminophen curve 22 increases to a value at 0.6V approximately equal to the value of the hydrogen peroxide signal at that same bias potential, after which the acetaminophen curve 22 continues to increase at a slightly slower rate.

The total signal 24 shows the curve that can be obtained by exposing an electrochemical sensor to glucose and acetaminophen. It is particularly noted that at 0.6 V, acetaminophen adds significantly to the signal output, which cause erroneously high readings of the glucose concentration when a presence or amount of acetaminophen is unknowingly introduced. In other words, the output signal of an electrochemical sensor may not be indicative of the actual glucose concentration due to signal interference from acetaminophen. Therefore, the preferred embodiments provide systems and methods for identifying the presence of an interfering species and optionally deriving and analyte value therefrom.

In general, the preferred embodiments measure the difference between the sensor signal at low and high bias potential settings, hereinafter referred to as the "differential measurement," which at the minimum enables identification of signal contribution from the interfering species. A differential measurement that is relatively low or shows substantial equivalence (for example, below a set threshold) identifies a substantially glucose-only signal. In contrast, a differential measurement that is relatively higher or does not show substantial equivalence (for example, above a set threshold) identifies the presence of interfering species (for example, acetaminophen) on a glucose signal.

In some embodiments, the differential measurement can be obtained from a single analyte-measuring device with multiple sensors. In one such example, the first sensor can be biased at a voltage of about +0.4V and the second sensor can be biased at a voltage about +0.6V. The two sensors can be provided under the same membrane system or separate membrane systems. The two sensors can share the same reference and/or counter electrodes or can utilize separate reference and/or counter electrodes.

In some embodiments, the differential measurement can be obtained by switching the bias potential of a single sensor between the two measurement potentials. The bias potentials can be held at each respective setting (high and low bias settings) for as short as milliseconds to as long as minutes or hours. Pulsed amperometric detection (PED) is one method of quickly switching voltages, such as described in Bisenberger, M.; Brauchle, C.; Hampp, N. A triple-step potential waveform at enzyme multisensors with thick-film gold electrodes for detection of glucose and sucrose. *Sensors and Actuators* 1995, B, 181–189, which is incorporated herein by reference in its entirety. In some embodiments, bias potential settings are held long enough to allow equilibration.

Figure 3:
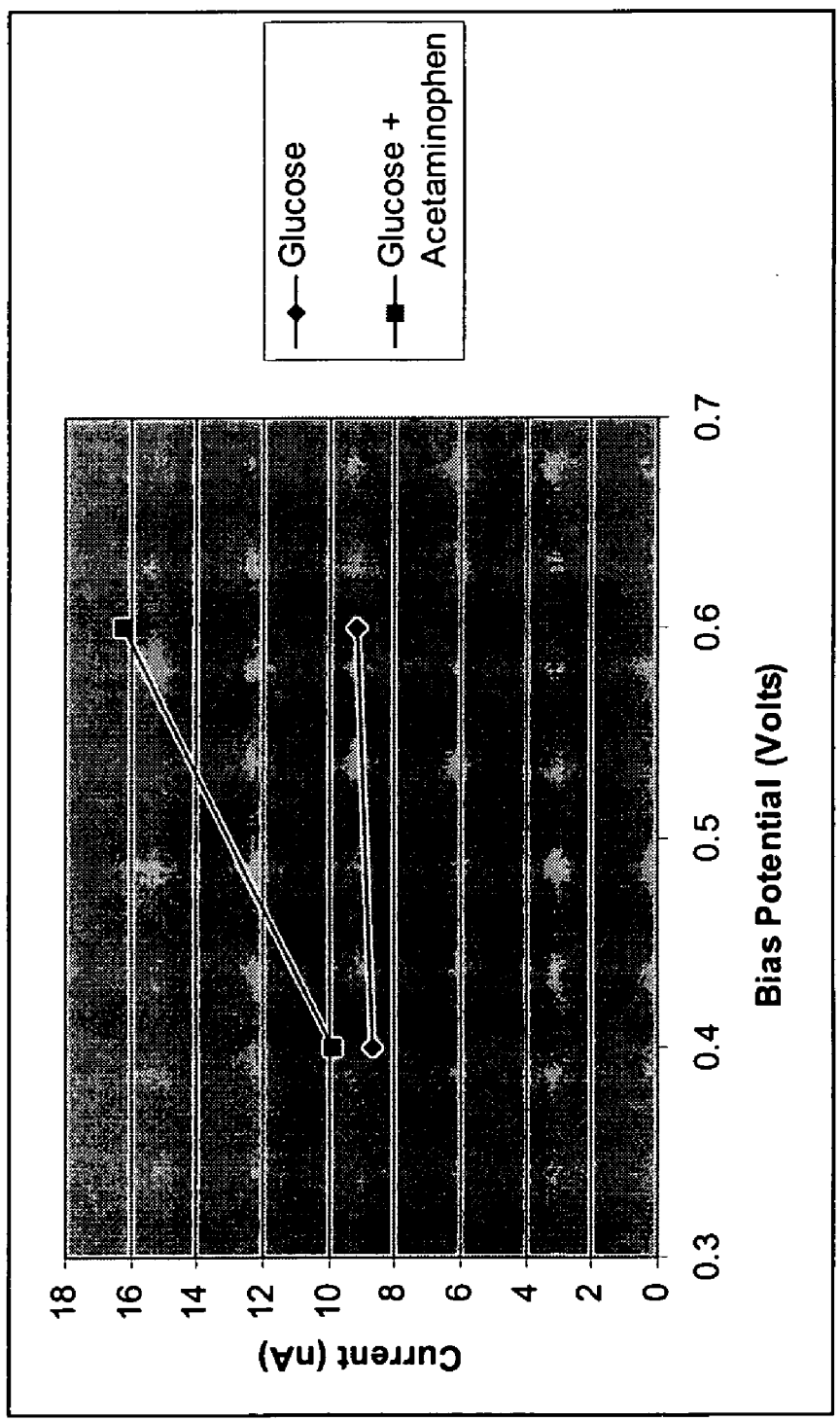
FIG. 3 is a graph that shows the effects of bias potential on the measurement of glucose and acetaminophen.

FIG. 3 is a graph that illustrates an experiment wherein acetaminophen was identified as an interfering species during glucose measurements. The experiment measured glucose and glucose with acetaminophen at different bias potential settings. The x-axis represents bias potential (V); the y-axis represents the sensor signal (current) measured by the sensor in nanoAmps (nA). The glucose sensor was constructed such as described in U.S. Pat. No. 6,001,067 and U.S. Published Patent Application 2003-0032874 A1, which are incorporated herein by reference in their entirety.

Initially, the glucose sensor was set with a bias potential of about +0.6V and placed in a solution with a glucose concentration of 400 mg/dL (no acetaminophen). The resulting current output was about 9.2 nA. Then, the bias potential of the glucose sensor was set to +0.4V and maintained with the sensor in the 400-mg/dL glucose solution. The resulting current output settled at about 8.7 nA.

Next, 3.0 mg/dL acetaminophen was added to the 400 mg/dL glucose solution with the +0.4V bias potential maintained on the sensor. The resulting current output increased slightly and settled at about 9.9 nA. Finally, the bias potential was returned to +0.6V while the glucose sensor remained in the glucose and acetaminophen solution. The resulting current output settled at about 16.2 nA.

Table 1 shows a comparison of the signal at the two bias potentials in the presence of glucose only and in the presence of glucose and acetaminophen. A small differential measurement is observed in the presence of glucose only (about 0.5 nA or 6%). In contrast, a large differential measurement is observed in the presence of glucose and acetaminophen (about 6.3 nA or 71%). Therefore, by measuring current at +0.4 V and +0.6 V bias, a quality assessment of the glucose measurement can be obtained from the measurement differential (delta) in current.

TABLE 1

| Bias | Glucose | Glucose and Acetaminophen |
| --- | --- | --- |
| +0.4 V | 8.7 nA | 9.9 nA |
| +0.6 V | 9.2 nA | 16.2 nA |
| Differential Measurement | 0.5 nA | 6.3 nA |

In some embodiments, the device can utilize the differential measurements as a measure of accuracy for the device. If interfering species (for example, acetaminophen or interference from low oxygen, for example) is observed, the device can be programmed to discontinue glucose information to the patient until an insignificant differential measurement is restored, for example.

In some embodiments, when the device measures a level of inaccuracy, the signal measurements can be adjusted to provide a more accurate glucose signal. Namely, the measured difference in current between the signals can be utilized to calculate the glucose signal without the interfering species. For example, the following first and second equations represent the relationship between the glucose and acetaminophen signal at first and second bias potentials, respectively:

$$Y_{0.4V} = \alpha[A] + \beta[B] \quad \text{(Equation 1)}$$

$$Y_{0.6V} = \delta[A] + \gamma[B] \quad \text{(Equation 2)}$$

In these equations, Y represents the total current of the signal output of the sensor in nanoAmps at each respective bias potential setting, [A] represents the concentration of glucose, [B] represents the concentration of acetaminophen, and $\alpha$, $\beta$, $\delta$, and $\gamma$ represent constants associated with glucose and acetaminophen at each respective bias potential setting. When these constants are known, glucose measurements can be taken at 0.4V and 0.6V, after which Equations 1 and 2 can be solved to determine the signal concentration due to glucose and acetaminophen separately, thereby enabling the reporting of the true glucose signal.

In some embodiments, these constants ($\alpha$, $\beta$, $\delta$, and $\gamma$) can be obtained by in vitro and/or in vivo calibration. In vitro calibration of $\alpha$ and $\delta$ can be accomplished by measuring a sensor exposed to a known concentration of glucose solution [A] (namely, without acetaminophen) at bias potential settings of 0.4V and 0.6V to obtain $Y_{0.4V}$ and $Y_{0.6V}$, respectively; by knowing [A], $Y_{0.4V}$, and $Y_{0.6V}$, the glucose-specific portions of Equations 1 and 2 ($Y_{0.4V} = \alpha[A]$ and $Y_{0.6V} = \delta[A]$) can be solved to determine $\alpha$ and $\delta$. Similarly, in vitro calibration of $\beta$ and $\gamma$ can be accomplished by measuring a sensor exposed to a known concentration of acetaminophen solution [B] (namely, without glucose) at bias potential settings of 0.4V and 0.6V to obtain $Y_{0.4V}$ and $Y_{0.6V}$, respectively; by knowing [B], $Y_{0.4V}$, and $Y_{0.6V}$, the acetaminophen-specific portions of Equations 1 and 2 ($Y_{0.4V} = \beta[B]$ and $Y_{0.6V} = \gamma[B]$) can be solved to determine $\beta$ and $\gamma$.

In some embodiments, the device can benefit from in vivo calibration of the constants. In one such example, an acetaminophen-free in vivo environment is created. The glucose concentration is then measured (for example, using a blood glucose meter, Yellow Springs Instrument (YSI), or the like), from which $\alpha$ and $\delta$ can be calculated such as described with reference to the in vitro glucose constants calibration, above. Similarly, acetaminophen constants $\beta$ and $\gamma$ can be calculated empirically (in vivo) and the ratio of glucose constants ($\alpha$ and $\delta$) to acetaminophen constants ($\beta$ and $\gamma$) in vivo can be determined. Using the known ratio of glucose constants to acetaminophen constants, Equations 1 and 2 can be solved to determine the glucose signal without the interfering species.

While certain examples of calibration in vitro and in vivo have been provided, other calibration methods can be applied to the preferred embodiments to determine glucose and acetaminophen concentrations. Additionally, although specific examples have been drawn toward a glucose sensor that eliminates acetaminophen as an interfering species, the concepts can by applied to other analyte sensors with other interfering species. Furthermore, multiple (more than two) analytes and/or interfering species can be determined using the concepts described here by increasing the number of measurements taken. Even more, the bias potentials settings can be altered and/or optimized using information obtained from CV-curve for the various analytes being measured.

In some embodiments, Equations 1 and 2 can further include a baseline, (for example, ($Y_{0.4V} = \alpha[A] + \beta[B] + C$) and ($Y_{0.6V} = \delta[A] + \gamma[B] + C$)). However, in some embodiments, other processes can be used to compensate for baseline (for example, during calibration of the sensor).

While not wishing to be bound by theory, it is believed that a wide variety of interfering species for a wide variety of analyte-measuring devices can utilize methods described herein, including comparing current values at multiple bias potential settings to assess the quality of the analyte measurement, identify interfering species, and calculate substantially interference-free analyte concentration measurements.

In some embodiments, periodic or regular cyclic voltammograms are performed (scanned) to determine information about a variety of interferants based on the shape of the curve or the data that forms the curve. This embodiment can be advantageous for determining the optimal bias potential setting for measurement of the analyte of interest, or settings for identifying and/or reducing signal effects of one or multiple interferants. Additionally, this embodiment provides a means by which the sensor can periodically or regularly scan for a variety of transient interferants (for example, acetaminophen).

In another aspect of the preferred embodiments, measurements taken at different bias potential settings are used to measure interference in the signal due to low oxygen levels. In one embodiment, $H_2O_2$ concentration (analyte byproduct of glucose and oxygen) is measured with a first bias potential (for example, about 0.6V). The $O_2$ concentration can then be measured at a second bias potential that is set much lower than the first (for example, about −0.6V). In practice, the first bias potential can be set to measure $H_2O_2$ on a regular basis, while the second bias potential measures $O_2$ periodically or intermittently (for example, about −0.6 V). The first and second measurements can be made using two distinct sensors or by switching the bias potential of one sensor, for example using pulsed amperometric detection (PED). In one such example, the first and second bias potentials can be set by controlling the reference electrode set potential using a resistor switch network, digital-to-analog converter (DAC), or the like.

Consequently in this alternative embodiment, by monitoring both $H_2O_2$ and $O_2$, including one analyte being measured either on demand or on both analytes being measured periodically, the two measurements can be utilized to determine interference due to transient ischemic conditions, for example. Namely, local ischemia can affect sensor performance in vivo due to low $O_2$ levels that compromise the glucose oxidase reaction and thus signal output of the sensor. If a simultaneous drop of sufficient magnitude and rate are noticed in both signals, an ischemic event is likely occurring. If a drop in $H_2O_2$ (namely, of sufficient magnitude and rate) is noticed without a similar drop in $O_2$, then no ischemic event is likely, but rather a true glucose concentration change. Conversely, if a drop in $O_2$ (namely, of sufficient magnitude and rate) is noticed without a similar drop in $H_2O_2$, then an ischemic event is likely, but not significant enough to compromise the integrity of the $H_2O_2$ measurement via the glucose oxidase reaction. Consequently, detection of low $O_2$ (ischemia) and its resulting effects on the sensor signal output can be used to cease data output (for example, because the output may be erroneous and result in misdiagnosis), trigger a message to the user (for example, to suggest a change of position and/or caution them about the data output), or compensate for the signal loss due to the effects of local ischemia (for example, using algorithms that measure and eliminate the signal error due to ischemia).

While the methods herein have been described in relation to acetaminophen as an interfering species, the methods can be modified so as to apply to a wide variety of interfering species and to a wide variety of analyte-measuring devices.

Methods and devices that are suitable for use in conjunction with aspects of the preferred embodiments are disclosed in copending U.S. application Ser. No. 10/695,636 filed Oct. 28, 2003 and entitled, "SILICONE COMPOSITION FOR BIOCOMPATIBLE MEMBRANE"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. application Ser. No. 09/916,386 filed Jul. 27, 2001 and entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE." All of the above references are incorporated by reference herein in their entirety.

The above description provides several methods and materials of the invention. This invention is susceptible to modifications in the methods and materials, as well as alterations in the fabrication methods and equipment. Such modifications will become apparent to those skilled in the art from a consideration of this application or practice of the invention provided herein. Consequently, it is not intended that this invention be limited to the specific embodiments provided herein, but that it cover all modifications and alternatives coming within the true scope and spirit of the invention as embodied in the attached claims. All patents, applications, and other references cited herein are hereby incorporated by reference in their entirety.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

What is claimed is:

1. A method for identifying an interfering species using an analyte-measuring device, the method comprising:
   providing at least one electrochemical sensor;
   measuring a first signal output obtained at a first bias potential setting;
   measuring a second signal output obtained at a second bias potential setting;
   comparing the first signal output with the second signal output to determine a differential measurement, thereby identifying a presence of an interfering species in a liquid; and
   calculating an analyte concentration from the differential measurement, wherein the step of calculating is performed when interfering species are positively identified, and wherein the interfering species are positively identified when the differential measurement is above a set threshold.

2. The method of claim 1, wherein the sensor is configured to switch between the first bias potential setting and the second bias potential setting.

3. The method of claim 1, wherein the step of providing comprises providing a first sensor at the first bias potential setting and a second sensor at the second bias potential setting.

4. The method of claim 1, wherein the interfering species is acetaminophen.

5. The method of claim 1, wherein the analyte measuring device is a glucose sensor.

6. The method of claim 1, wherein the liquid is a bodily fluid.

7. The method of claim 1, wherein the bodily fluid is interstitial fluid.

8. The method of claim 1, wherein the liquid is interstitial fluid, the analyte measuring device is a glucose sensor, and the interfering species is acetaminophen.

9. The method of claim 1, further comprising a step of calibrating the electrochemical sensor in vivo.

10. The method of claim 1, further comprising a step of calibrating the electrochemical sensor in vitro.

11. The method of claim 1, further comprising a step of measuring a concentration of at least one additional analyte at at least one additional bias potential setting.

12. The method of claim 1, further comprising a step of obtaining at least one cyclic voltammogram to measure at least one interfering species concentration.

13. The method of claim 1, further comprising a step of determining an optimal bias potential setting for measurement of the analyte concentration.

14. The method of claim 1, further comprising a step of measuring a third signal output at a third bias potential setting, wherein the third signal output identifies an interference in the analyte concentration due to a low oxygen level.

15. A method for identifying an interfering species using an analyte-measuring device, the method comprising:
   providing at least one electrochemical sensor;
   measuring a first signal output obtained at a first bias potential setting;
   measuring a second signal output obtained at a second bias potential setting;
   comparing the first signal output with the second signal output to determine a differential measurement, thereby identifying a presence of an interfering species in a liquid; and deriving an analyte concentration from the first signal output and the second signal output to determine an analyte concentration.

16. The method of claim 15, wherein the sensor is configured to switch between the first bias potential setting and the second bias potential setting.

17. The method of claim 15, wherein the step of providing comprises providing a first sensor at the first bias potential setting and a second sensor at the second bias potential setting.

18. The method of claim 15, wherein the interfering species is acetaminophen.

19. The method of claim 15, wherein the analyte measuring device is a glucose sensor.

20. The method of claim 15, wherein the liquid is a bodily fluid.

21. The method of claim 15, wherein the bodily fluid is interstitial fluid.

22. The method of claim 15, wherein the liquid is interstitial fluid, the analyte measuring device is a glucose sensor, and the interfering species is acetaminophen.

23. The method of claim 15, further comprising a step of calibrating the electrochemical sensor in vivo.

24. The method of claim 15, further comprising a step of calibrating the electrochemical sensor in vitro.

25. The method of claim 15, further comprising a step of measuring a concentration of at least one additional analyte at at least one additional bias potential setting.

26. The method of claim 15, further comprising a step of obtaining at least one cyclic voltammogram to measure at least one interferent concentration.

27. The method of claim 15, further comprising a step of determining an optimal bias potential setting for measurement of the analyte concentration.

28. The method of claim 15, further comprising steps of measuring a third signal output at a third bias potential setting, wherein the third signal output identifies an interference in the analyte concentration due to a low oxygen level.

29. A method for identifying a signal interference in an analyte-measuring device, the method comprising:
providing at least one electrochemical sensor;
measuring a first signal output obtained at a first bias potential setting;
measuring a second signal output at a second bias potential setting;
comparing the first signal output with the second signal output to determine a differential measurement, thereby identifying an interference in the signal outputs; and
deriving an analyte concentration from the first signal output and the second signal output to determine an analyte concentration.

30. The method of claim 29, further comprising measuring a third signal output at a third bias potential setting indicative of an additional interference in the signal outputs.

31. The method of claim 29, wherein the analyte comprises glucose and the interfering species comprises acetaminophen.

32. The method of claim 29, wherein the analyte comprises glucose.

33. The method of claim 29, wherein the interfering species comprises acetaminophen.

34. The method of claim 29, wherein the sensor is configured to switch between the first bias potential setting and the second bias potential setting.

35. The method of claim 29, wherein the step of providing comprises providing a first sensor at the first bias potential setting and a second sensor at the second bias potential setting.

36. The method of claim 29, further comprising a step of calibrating the electrochemical sensor in vivo.

37. The method of claim 29, further comprising a step of calibrating the electrochemical sensor in vitro.

38. The method of claim 29, further comprising a step of measuring a concentration of at least one additional analyte at at least one additional bias potential setting.

39. The method of claim 29, further comprising a step of obtaining at least one cyclic voltammogram to measure at least one interferent concentration.

40. The method of claim 29, further comprising a step of determining an optimal bias potential setting for measurement of the analyte concentration.

41. The method of claim 29, wherein the interference in the signal outputs is due to a low oxygen level.

42. The method of claim 29, further comprising a step of measuring a third signal output at a third bias potential setting; wherein the third signal output identifies an interference in the analyte concentration due to a low oxygen level.

* * * * *

UNITED STATES PATENT AND TRADEMARK OFFICE
CERTIFICATE OF CORRECTION

PATENT NO. : 7,081,195 C1
APPLICATION NO. : 90/011645
DATED : April 24, 2012
INVENTOR(S) : Simpson et al.

It is certified that error appears in the above-identified patent and that said Letters Patent is hereby corrected as shown below:

NOTE: Title page, item 73 should read DexCom as detailed:

In the Copy of patent for which reexamination is requested (06/01/2011), Assignee Name is given as:

"DexCom, inc., San Diego, CA (US)"

whereas in the Ex-Parte Reexamination Certificate, Assignee Name is given as:

"Dexcom, Inc., San Diego, CA (US)"

Please capitalize the "C" in DexCom, Inc.

| Issued Patent | | Description of Discrepancy |
|---|---|---|
| Column | Line | |
| 1 | 55 | In Claim 26, change "cycle" to --cyclic--. |
| 2 | 36 | In Claim 46, change "concentraton" to --concentration--. |

Signed and Sealed this
Twenty-fifth Day of September, 2012

David J. Kappos
*Director of the United States Patent and Trademark Office*

(12) EX PARTE REEXAMINATION CERTIFICATE (8984th)
United States Patent
Simpson et al.

(10) Number: US 7,081,195 C1
(45) Certificate Issued: Apr. 24, 2012

(54) SYSTEMS AND METHODS FOR IMPROVING ELECTROCHEMICAL ANALYTE SENSORS

(75) Inventors: Peter Simpson, Del Mar, CA (US); James Brauker, San Diego, CA (US); Victoria Carr-Brendel, Pleasanton, CA (US); Paul Goode, Cherry Hill, NJ (US); Mark Tapsak, Orangeville, PA (US)

(73) Assignee: Dexcom, Inc., San Diego, CA (US)

Reexamination Request:
No. 90/011,645, Apr. 14, 2011

Reexamination Certificate for:
Patent No.: 7,081,195
Issued: Jul. 25, 2006
Appl. No.: 11/007,635
Filed: Dec. 7, 2004

Related U.S. Application Data

(60) Provisional application No. 60/614,683, filed on Sep. 30, 2004, provisional application No. 60/587,787, filed on Jul. 13, 2004, and provisional application No. 60/527,892, filed on Dec. 8, 2003.

(51) Int. Cl.
*G01N 27/327* (2006.01)
*G01N 27/26* (2006.01)
*A61B 5/00* (2006.01)

(52) U.S. Cl. .................. 205/777.5; 204/403.01; 204/403.11; 205/792

(58) Field of Classification Search .................. None
See application file for complete search history.

(56) References Cited

To view the complete listing of prior art documents cited during the proceeding for Reexamination Control Number 90/011,645, please refer to the USPTO's public Patent Application Information Retrieval (PAIR) system under the Display References tab.

*Primary Examiner* — Alan Diamond

(57) ABSTRACT

An analyte-measuring device, particularly an electrochemical sensor, is provided for measuring current values at multiple bias potential settings to assess the quality of the analyte measurement, identify interference in the signal, and calculate substantially interference-free analyte concentration measurements. The device and method are suitable for calculating substantially interference-free analyte concentration measurements when glucose is the analyte and acetaminophen is an interfering species.

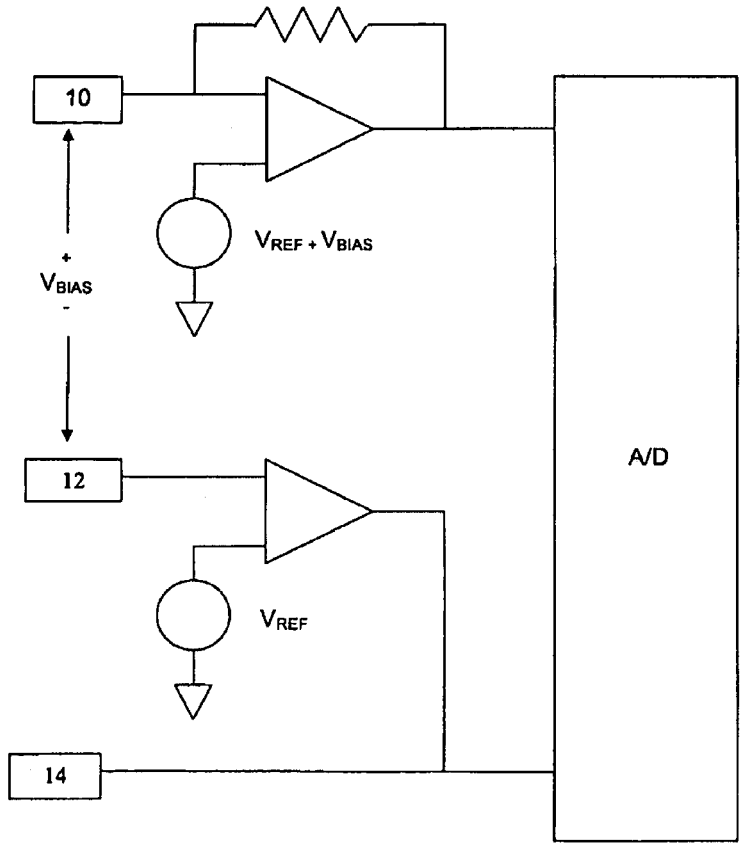

US 7,081,195 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 4, 9, 17, 18, 23, 35 and 36 is confirmed.

Claims 1, 15 and 29 are cancelled.

Claims 2, 5, 6, 10, 12, 13, 16, 19, 20, 24, 26, 27, 31-34, 37, 39 and 40 are determined to be patentable as amended.

New claims 43-62 are added and determined to be patentable.

Claims 7, 8, 11, 14, 21, 22, 25, 28, 30, 38, 41 and 42 were not reexamined.

2. The method of claim [1] *51*, wherein the sensor is configured to switch between the first bias potential setting and the second bias potential setting.

5. The method of claim [1] *51*, wherein the analyte measuring device is a glucose monitor.

6. The method of claim [1] *51*, wherein the liquid is bodily fluid.

10. The method of claim [1] *51*, further comprising a step of calibrating the electrochemical sensor in vitro.

12. The method of claim [1] *51*, further comprising a step of obtaining at least one cyclic voltammogram to measure at least one interfering species concentration.

13. The method of claim [1] *51*, further comprising a step of determining an optimal bias potential setting for measurement of the analyte concentration.

16. The method of claim [15] *52*, wherein the sensor is configured to switch between the first bias potential setting and the second bias potential setting.

19. The method of claim [15] *52*, wherein the analyte measuring device is a glucose sensor.

20. The method of claim [15] *52*, wherein the liquid is a bodily fluid.

24. The method of claim [15] *52*, further comprising a step of calibrating the electrochemical sensor in vitro.

26. The method of claim [15] *52*, further comprising a step of obtaining at least one cycle voltammogram to measure at least one interferent concentration.

27. The method of claim [15] *52*, further comprising a step of determining an optimal bias potential setting for measurement of the analyte concentration.

31. The method of claim [29] *53*, wherein the analyte comprises glucose and the *interference is caused by an* interfering species comprising acetaminophen.

32. The method of claim [29] *53*, wherein the analyte comprises glucose.

33. The method of claim [29] *53*, wherein the *interference is caused by an* interfering species comprising acetaminophen.

34. The method of claim [29] *53*, wherein the sensor is configured to switch between the first bias potential setting and the second bias potential setting.

37. The method of claim [29] *53*, further comprising a step of calibrating the electrochemical sensor in vitro.

39. The method of claim [29] *53*, further comprising a step of obtaining at least one cyclic voltammogram to measure at least one interferent concentration.

40. The method of claim [29] *53*, further comprising a step of determining an optimal bias potential setting for measurement of the analyte concentration.

*43. The method of claim 29, wherein the electrochemical sensor is a transcutaneous sensor.*

*44. The method of claim 29, wherein the first bias potential setting is +0.6V and the second bias potential setting is −0.6V.*

*45. The method of claim 29, wherein the first bias potential setting and the second bias potential setting are each maintained for less than one second.*

*46. The method of claim 29, wherein a first equation and a second equation represent a relationship between the analyte concentration and the interference at the first and second bias potential settings, respectively, wherein the first equation is defined as*

$$Y_{first} = \alpha[A] + \beta[B],$$

*wherein the second equation is defined as*

$$Y_{second} = \delta[A] + \gamma[B],$$

*wherein Y represents a total current of the signal output of the sensor in terms of current at each respective first and second bias potential setting, [A] represents the concentraton of the analyte, [B] represents a concentration of an interfering species, α and β represent constants associated with the analyte and the interference, respectively, at the first bias potential setting, and δ and γ represent constants associated with the analyte and interference, respectively, at the second bias potential setting.*

*47. The method of claim 46, wherein the constants α, β, δ and γ are obtained based on in vitro calibration.*

*48. The method of claim 46, wherein the constants α, β, δ and γ are obtained based on in vivo calibration.*

*49. The method of claim 29, wherein a first equation and a second equation represent a relationship between the analyte concentration and the interference at the first and second bias potential settings, respectively, wherein the first equation is defined as*

$$Y_{first} = \alpha[A] + \beta[B] + C,$$

*wherein the second equation is defined as*

$$Y_{second} = \delta[A] + \gamma[B] + C,$$

*wherein Y represents a total current of the signal output of the sensor in terms of current at each respective first and second bias potential setting, [A] represents the concentration of the analyte, [B] represents a concentration of an interference, C represents a baseline, α and β represent constants associated with the analyte and the interference, respectively, at the first bias* potential setting, and δ and γ represent constants associated with the analyte and the interference, respectively, at the second bias potential setting.

50. The method of claim 29, wherein the second signal output is representative of an oxygen level, and wherein deriving the analyte concentration comprises compensating for the effects of an insufficient level of oxygen.

51. A method for identifying an interfering species using an analyte-measuring device, the method comprising:
providing at least one electrochemical sensor;
measuring a first signal output obtained at a first bias potential setting;
measuring a second signal output obtained at a second bias potential setting;
comparing the first signal output with the second signal output to determine a differential measurement, thereby identifying a presence of an interfering species in a liquid; and
calculating an analyte concentration from the differential measurement, wherein the step of calculating is performed when interfering species are positively identified, and wherein the interfering species are positively identified when the differential measurement is above a set threshold,
wherein the first bias potential setting is at a different bias voltage than the second bias potential setting.

52. A method for identifying an interfering species using an analyte-measuring device, the method comprising:
providing at least one electrochemical sensor;
measuring a first signal output obtained at first bias potential setting;
measuring a second signal output obtained at a second bias potential setting;
comparing the first signal output with the second signal output to determine a differential measurement, thereby identifying a presence of an interfering species in a liquid; and
deriving an analyte concentration from the first signal output and the second signal output to determine an analyte concentration,
wherein the first bias potential setting is at a different bias voltage than the second bias potential setting.

53. A method for identifying a signal interference in an analyte-measuring device, the method comprising:
providing at least one electrochemical sensor;
measuring a first signal output obtained at a first bias potential setting;
measuring a second signal output at a second bias potential setting;
comparing the first signal output with the second signal output to determine a differential measurement, thereby identifying an interference in the signal outputs; and
deriving an analyte concentration from the first signal output and the second signal output to determine an analyte concentration,
wherein the first bias potential setting is at a different bias voltage than the second bias potential setting.

54. The method of claim 53, wherein the electrochemical sensor is a continuous glucose sensor.

55. The method of claim 53, further comprising measuring changes in glucose concentration over time using the electrochemical sensor.

56. The method of claim 53, wherein the first bias potential setting is +0.4V and the second bias potential setting is +0.6V.

57. The method of claim 53, wherein the first bias potential setting is lower than the second bias potential setting.

58. The method of claim 53, wherein a differential in current between the first signal and the second signal is used to derive the analyte concentration substantially without the interference.

59. The method of claim 53, wherein the electrochemical sensor is a glucose oxidase-based sensor.

60. The method of claim 53, wherein the first signal output is a current change induced by $H_2O_2$ and any interfering species with an oxidation or reduction potential that overlaps with $H_2O_2$, and wherein the current change induced by $H_2O_2$ is representative of the analyte concentration.

61. The method of claim 53, wherein the method of claim 53 is performed periodically or regularly using the sensor.

62. The method of claim 53, further comprising regularly measuring a signal output at the first bias potential and regularly or intermittently measuring a signal output at the second bias potential.

* * * * *